United States Patent [19]

Cohen

[11] Patent Number: 4,625,237

[45] Date of Patent: Nov. 25, 1986

[54] METHOD FOR DETECTING BLEMISHES CONTIGUOUS TO THE PERIMETER OF A CCD IMAGE

[75] Inventor: Edward Cohen, Lancaster, Pa.

[73] Assignee: RCA Corporation, Princeton, N.J.

[21] Appl. No.: 663,153

[22] Filed: Oct. 22, 1984

[51] Int. Cl.[4] .................................. H04N 7/18
[52] U.S. Cl. ........................................ 358/106
[58] Field of Search ............... 358/213, 212, 106, 209, 358/139, 10, 163; 382/8

[56] References Cited

U.S. PATENT DOCUMENTS 4,454,541 6/1984 Duschl ................................ 358/106
4,454,545 6/1984 Duschl ................................ 358/213

FOREIGN PATENT DOCUMENTS 2102122 1/1983 United Kingdom ............... 358/106

*Primary Examiner*—Gene Z. Rubinson
*Assistant Examiner*—Stephen Brinich
*Attorney, Agent, or Firm*—E. M. Whitacre; D. H. Irlbeck; L. L. Hallacher

[57] ABSTRACT

Blemishes in the proximity of the perimeter of an image on a charge coupled device (CCD) are detected. The image pixels adjacent to the perimeter are sequentially detected and three consecutive pixels define a motion as either straight, clockwise or counterclockwise. The detection occurs in a clockwise direction and straight or clockwise motions are permitted. When two counterclockwise motions are detected, and a clockwise motion has not occurred between them, a blemish signal is provided.

6 Claims, 7 Drawing Figures

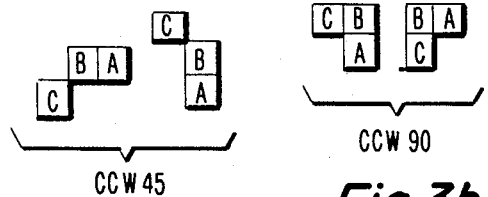
Fig.3a  Fig.3b  Fig.4
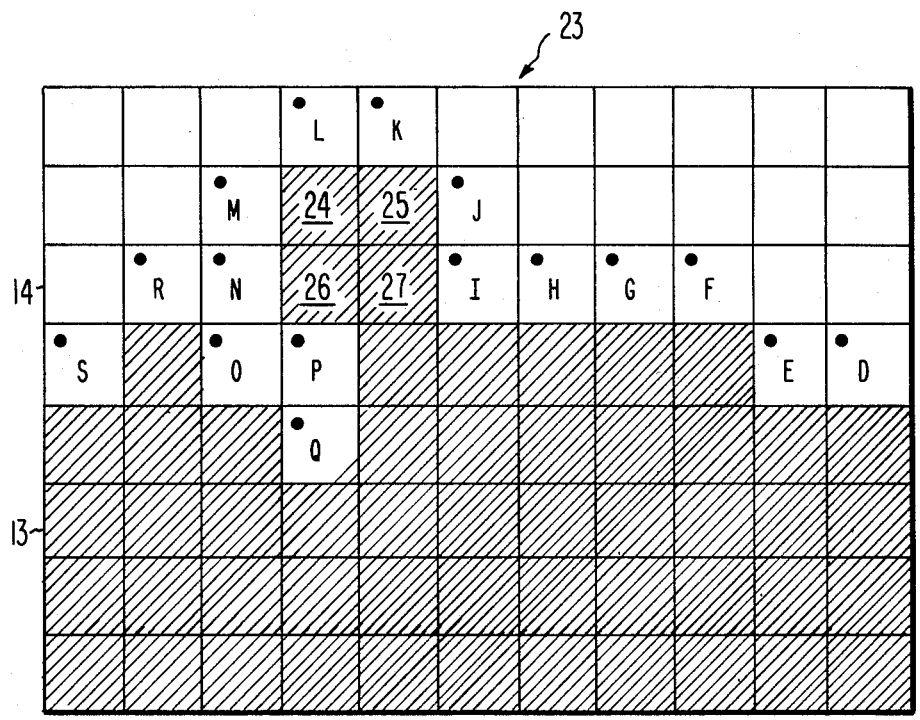
Fig.5

METHOD FOR DETECTING BLEMISHES CONTIGUOUS TO THE PERIMETER OF A CCD IMAGE

BACKGROUND

This invention relates generally to CCD (charge coupled device) imaging and particularly to a method for detecting blemishes contiguous to the perimeter of an image on a CCD.

U.S. Pat. No. 4,454,545 issued to R. A. Duschl discloses a CCD based inspection system.

U.S. Pat. No. 4,454,541 issued to R. A. Duschl discloses a system and method for detecting blemishes on the screen of a kinescope. Blemishes are detected by comparing the signal level on each CCD pixel with the average of the signals on the immediately adjacent pixels and generating a blemish signal when the difference exceeds a predetermined threshold.

U.S. Pat. No. 4,575,751 entitled "Method and Subsystem for Plotting the Perimeter of an Object" issued to R. A. Duschl, now U.S. Pat. No. 4,575,751, discloses a system for plotting the perimeter of an image cast onto a CCD. The image pixels immediately adjacent to the perimeter pixels are identified and their addresses held in memory irrespective of the orientation of the image and the size of the image.

U.S. application Ser. No. 663,699 entitled "Method for Avoiding Identifying Perimeter Variations As Blemishes in a CCD Image" filed on even date herewith by Edward Cohen discloses a method which can be used along with the present invention. The teachings of these patents and applications are incorporated herein by reference.

The systems described in the above-referenced application and patents are quite satisfactory for the purposes intended. However, difficulties sometime arise because a blemish in close proximity to the perimeter is identified as a portion of the perimeter and thus is not identified as a blemish which should result in the rejection of the object being inspected. For this reason, there is a need for a method for detecting blemishes in the close proximity of the perimeter of an image on a CCD. The present invention fulfills this long felt need.

The present invention is cast into the environment of detecting the perimeter of a black matrix on the inside surface of a CRT faceplate panel. This environment was selected when describing the present invention because the invention is an improvement of the inventions described in the referenced patents and patent applications and those inventions are described in that environment. Nevertheless it will be understood by those skilled in the art that the present invention is useful in detecting blemishes in the proximity of the perimeter of any image cast onto a CCD.

SUMMARY

In a method of detecting blemishes in the proximity of the perimeter of an image on the pixels of a charge coupled device (CCD), a motion direction for considering the pixels around the perimeter is selected. A motion is defined as the consideration of three consecutive pixels. Motions occurring in the selected direction and straight motions are permissible. Motions occurring in a direction opposite to the selected direction are defined as blemish motions. A blemish signal is provided when two blemish motions occur without an intervening motion in the selected direction.

BRIEF DESCRIPTION

FIGS. 3a and 3b show the counterclockwise motions which can result in the generation of a blemish signal.

FIG. 4 shows how the directions of the motions are defined.

FIG. 5 is an enlarged portion of the matrix perimeter of FIG. 1 showing how the pixels along the perimeter are sequentially considered to detect blemishes in the proximity of the perimeter.

DETAILED DESCRIPTION

Figure 1:
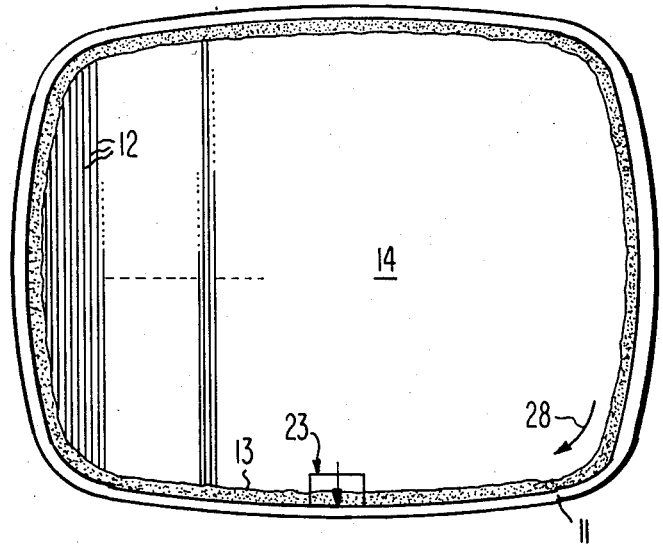
FIG. 1 shows the perimeter of the black matrix present on the inside surface of a faceplate panel.

In FIG. 1, the inside surface of a CRT faceplate panel 11 includes a black matrix which is composed of a plurality of parallel black lines 12 and a perimeter 13. The parallel lines 12 extend across the entire surface of the panel 11 and only several are shown for simplicity. Phosphors are arranged in the spaces between the matrix lines 12 in a sequential fashion and each phosphor emits a different color of light when impacted with electrons. Thus, the phosphors are arranged in a repetitive pattern such as red, green and blue across the entire inside surface of the panel 11 to form a screen 14.

Figure 2:
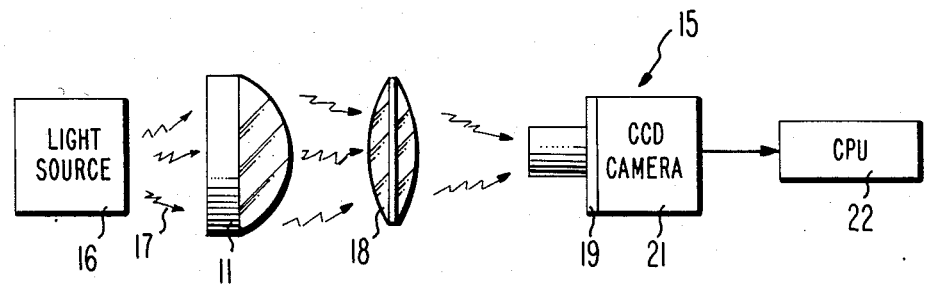
FIG. 2 is a simplified showing of a CCD based image inspection system.

FIG. 2 shows a CCD based inspection system 15 which can be of the type described in U.S. Pat. No. 4,454,545 and which can include the blemish detection system described in U.S. Pat. No. 4,454,541. The inspection system 15 includes a light source 16, the light rays 17 of which fully illuminate the phosphor screen 14 on the inside surface of the panel 11. The light rays 17 pass through the phosphor screen and are focused by a lens 18 onto the CCD 19 within a CCD camera 21. Each pixel of the CCD 19 in the camera 21 is charged to a particular level depending upon the amount of light received by the individual pixels. Thus, the pixels receiving light passing through the screen 14 are charged to a different level than the pixels shaded by the lines 12 and the perimeter 13. The pixel data are transferred from the CCD 19 to a central processing unit 22 and processed in accordance with the inspection being made. The inspection can be the detection of blemishes in the screen 14 as described in U.S. Pat. No. 4,454,545 while utilizing the perimeter plotting described in U.S. Pat. No. 4,575,751 referenced hereinabove. The detection of blemishes in the proximity of the perimeter 13 described hereinafter also is carried out in the CPU 22.

FIG. 5 is a greatly magnified view of the rectangular portion 23 of the perimeter 13 of FIG. 1. In FIG. 5, the cross-hatched blocks represent pixels which are shaded by the perimeter 13. The clear blocks represent pixels receiving light through the phosphor screen 14. The pixels alphabetically labeled D to S and containing a dot in the upper left-hand corner represent the pixels which are identified as bordering the perimeter 13 utilizing the perimeter plotting described in U.S. Pat. No. 4,575,751. The pixels 24 to 27 received an energy level indicating that they are part of the perimeter 13 and are identified as such by the perimeter plotting system, as evidenced by the pixels I to N. However, these pixels are representative of a blemish which would be objectionable to a viewer and thus should have been identified as a blemish rather than as a part of the perimeter 13. The identification of the blemish represented by pixels 24 to 27 is accomplished by sequentially considering the charge levels on the perimeter defining pixels while progressing around the perimeter 13 in a preselected direction and consistently following a set of conventions. In FIG. 1, the preselected direction is selected to be clockwise, as represented by the arrow 28. The first convention is that of defining a motion as the consideration of three adjacent pixels. The second convention is the defining of adjacent pixels as two pixels having contiguous sides or having contiguous corners. The third convention is that of permitting any number of clockwise turning motions or straight motions but providing a blemish indication upon the occurrence of two counterclockwise turning motions without an intervening clockwise turning motion. The fourth convention defines the directions of the motions. The consideration of two adjacent pixels defines a pixel direction. Accordingly, each motion direction includes two pixel directions because each motion includes three pixels.

FIG. 3a shows two counterclockwise 45° turning motions progressing from pixel A to pixel C. FIG. 3b shows two counterclockwise 90° motions when progressing from pixel A to pixel C. The detection of any combination of two of the turning motions shown in FIG. 3a and 3b generates a blemish indication unless a clockwise turning motion has occurred between the two counterclockwise motions.

In FIG. 4, a central pixel 29 is surrounded by adjacent pixels 0 to 7 which are surrounded by pixels 30 to 45. When pixel 29 is the first pixel of a motion, any of the pixels 0 to 7 can be the second pixel of the motion. The third pixel of the motion will then be any of the pixels 0 to 7 or 30 to 45 which is adjacent to the second pixel and which has not already been considered. The directions of the pixel to pixel considerations, i.e., the pixel directions, are dependent upon the position of pixel 29 with respect to the perimeter 13. In FIG. 1, the selected direction defined by the arrow 28 is clockwise. Accordingly, when pixel 29 is positioned within the rectangular portion 23, consideration of pixels 29 to 3 results in a 45° pixel direction and consideration of pixels 3 to 43 a straight pixel direction. These two pixel directions combine into a motion direction away from the selected clockwise direction and thus the motion direction along the three pixels is counterclockwise. Consideration of pixels 29 to 5 to 45 results in a clockwise motion direction. Assuming that pixel 29 is located near the top portion of the perimeter 13, consideration of pixels 29 to 0 to 37 defines a clockwise motion direction and consideration of pixels 29 to 0 to 35 defines a counterclockwise motion direction. The consecutive consideration of three pixels contiguous at the corners, such as 29 to 7 to 34 defines a permissible straight motion direction. These straight motions are common going around the corners of the perimeter 13. The pixel directions are provided to the CPU 22 of FIG. 1 and used to calculate the motion directions.

FIG. 5 shows how the lettered pixels are sequentially detected in motions defined by sets of three pixels to detect the blemish indicated by the pixels 24 to 27. The enlarged portion 23 of the perimeter 13 is in the lower part of the perimeter, and therefore detection starts at the right of FIG. 5 and progresses to the left. The Table shows the motion directions defined by the sequential detection of the pixels D to L in sets of three.

TABLE

| PIXELS | MOTION DIRECTION |
|---|---|
| D-F | clockwise |
| E-G | counterclockwise |
| F-H | straight |
| G-I | straight |
| H-J | clockwise |
| I-K | counterclockwise |
| J-L | counterclockwise blemish indication |

Figure 6:
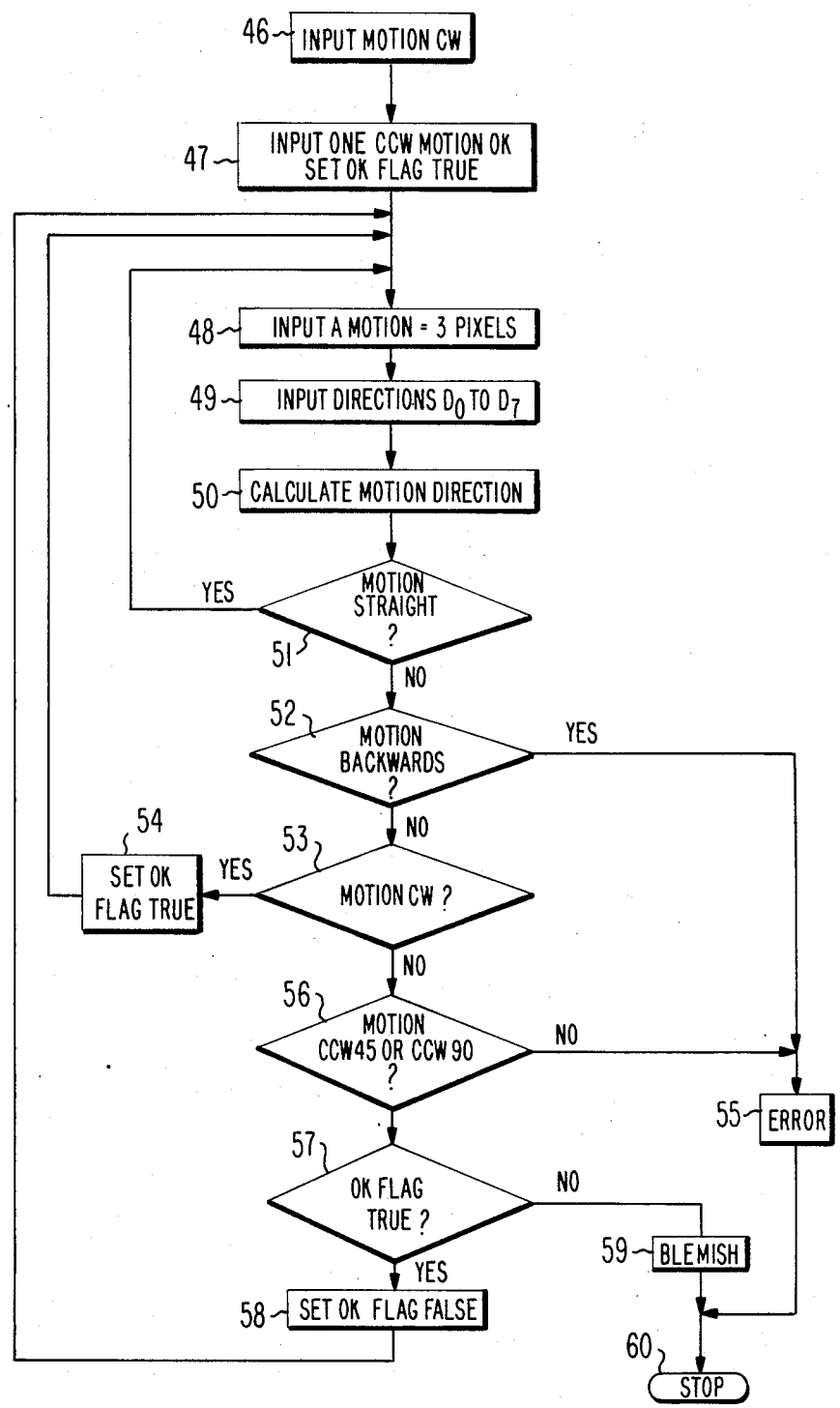
FIG. 6 is a flow chart of a preferred method of detecting blemishes in the proximity of the perimeter.

FIG. 6 is a flow chart showing how the CPU 22 of FIG. 2 is programmed to effect the blemish detection method described hereinabove. At step 46, the clockwise motion indicated by the arrow 28 of FIG. 1 is selected as the direction of detection of the energy levels on the perimeter defining pixels, e.g. D to S of FIG. 5. If desired a counterclockwise direction can be selected. However, when a counterclockwise direction is selected, a blemish is indicated by the detection of two clockwise motions without any intervening counterclockwise motions and all counterclockwise motions are permissible. At step 47, the permissibility of one counterclockwise motion is input to the CPU and the okay flag is set to true. The okay flag is used to record the detection of counterclockwise motions. At step 48 a motion is defined as three consecutive pixel detections. At step 49, the pixel directions are input to the CPU 22. In FIG. 4, assuming that pixel 29 is the pixel being detected, there are eight adjacent pixels 0 to 7. There, therefore, are eight possible pixel directions D0 to D7. The pixel direction to the adjacent pixel 0 to 7 which is a perimeter defining pixel is input to the CPU 22. Also, the direction from the pixel 0 to 7 to the third pixel 0 to 7 or 30 to 45 is input to the CPU 22. These two pixel directions are used to calculate the motion direction at step 50. The next motion direction is calculated using the last two of the preceeding three pixels. For example, assuming that pixels 29 to 0 to 7 determine a motion direction, the immediately succeeding motion direction is defined by pixels 0 to 7 and a pixel adjacent to pixel 7. The matrix shown in FIG. 4 is shifted so that pixel 0 is the central pixel and a new column of pixels is added to the matrix in place of the lefthand column of FIG. 4. Thus the matrix of FIG. 4 is shifted around the perimeter 13 and the pixel being considered is the central pixel. The orientation of the matrix remains unchanged and only the addresses of the pixels within the matrix are changed. These addresses are known from the perimeter defining system of U.S. Pat. No. 4,575,751.

At step 51, when the motion along the three consecutive pixels is straight, such as F, G and H of FIG. 5, step 48 is reentered and the next three pixels, e.g., G, H and I, are considered. When the motion is not straight, step 52 is entered to determine whether or not the motion is backwards. This step is utilized to verify that the motion is occurring in the selected direction and when the direction is wrong an error step 55 is entered to stop the routine at step 60. When the motion is not backwards at step 52, step 53 is entered to determine whether or not the motion is clockwise, e.g., along the pixels D, E and F of FIG. 5. When the motion is clockwise, the okay flag is verified as being set to true at step 54. When the motion is not clockwise, step 56 is entered to determine whether or not one of the four counterclockwise motions shown in FIGS. 3a and 3b has been detected. When the motion is counterclockwise, but is not one of those shown in FIG. 3a and 3b an error has occurred and the error step 55 is entered and the routine is stopped at step 60. When the counterclockwise motion is one of the permissible counterclockwise motions, step 57 is entered to verify that the okay flag is true. When the okay flag is true, the detected counterclockwise motion is the first one and step 58 is entered to set the okay flag false before returning to step 48 to investigate the next three consecutive pixels. When the okay flag is false at step 57, the counterclockwise motion results in a no answer and a blemish indication is given at step 59 and the routine is stopped at step 60. When a counterclockwise motion which sets the okay flag to false at step 58 is followed by a clockwise motion, the okay flag is reset to true at step 54 and, accordingly, single counterclockwise motions are permitted. However, straight motions do not reset the okay flag to true and therefore two consecutive counterclockwise motions, and two counterclockwise motions separated by only straight motions result in a blemish indication.

What is claimed is:

1. A method of detecting blemishes contiguous to the perimeter of an image on the pixels of a charge coupled device (CCD) comprising the steps of:
   sequentially detecting the charge levels on the pixels around said perimeter, said detecting occurring in a selected direction and consisting of a plurality of motions, wherein a motion is the detection of the charge levels on at least three consecutive pixels, and wherein straight motions and motions occurring in said selected direction are permissible, while motions in a direction opposite to said selected direction are blemish motions; and
   providing a blemish signal when two blemish motions occur and a motion in said selected direction has not occurred between said blemish motions.

2. The method of claim 1 wherein said selected direction is clockwise and said opposite direction is counterclockwise.

3. The method of claim 2 wherein said counterclockwise motions can be 45° and 90° motions.

4. The method of claim 1 wherein the direction of said motion is determined by two pixel motions, and each pixel motion is the detection of two adjacent pixels, and said two pixel motions occur on said three consecutive pixels.

5. A method of detecting blemishes in the proximity of the perimeter of an image on a charge coupled device (CCD) wherein said perimeter and said blemishes are indicated by CCD pixels charged to a first level and said image is indicated by CCD pixels charged to a second level comprising the steps of:
   consecutively detecting the energy level on the image pixels immediately adjacent to the pixels within said perimeter, said detecting occurring in a preselected direction on adjacent image pixels;
   recording the detection on three adjacent pixels as a motion in one of the three possible directions of straight, turning clockwise, or turning counterclockwise wherein one of said turning motions is in the same direction as said preselected direction; and
   providing a blemish indication when two turning motions in the direction different from said preselected direction are detected and a motion in said preselected direction has not occurred between said two turning motions.

6. The method of claim 5 wherein said turning motions can be 45° or 90° turns whereby two adjacent pixels can have contiguous sides and two adjacent pixels can have contiguous corners.

* * * * *